United States Patent
Hendriks et al.

(10) Patent No.: US 8,048,671 B2
(45) Date of Patent: Nov. 1, 2011

(54) TISSUE REPAIR WITH MULTIPOTENT CELLS

(75) Inventors: Jeanine Anna Alphonse Hendriks, Amerongen (NL); Mark Ewart De Bruijn, Utrecht (NL); Jens Uwe Riesle, Soest (NL)

(73) Assignee: Cellcotec B.V., Bilthoven (NL)

( * ) Notice: Subject to any disclaimer, the term of this patent is extended or adjusted under 35 U.S.C. 154(b) by 835 days.

(21) Appl. No.: 10/592,896

(22) PCT Filed: Mar. 18, 2005

(86) PCT No.: PCT/NL2005/000207
§ 371 (c)(1),
(2), (4) Date: Feb. 23, 2007

(87) PCT Pub. No.: WO2005/087239
PCT Pub. Date: Sep. 22, 2005

(65) Prior Publication Data
US 2007/0224172 A1    Sep. 27, 2007

(30) Foreign Application Priority Data
Mar. 18, 2004  (EP) .................................. 04075885

(51) Int. Cl.
C12N 5/00    (2006.01)
C12N 5/02    (2006.01)
(52) U.S. Cl. ......................... 435/373; 435/375; 435/377
(58) Field of Classification Search ................... 435/373, 435/375, 377
See application file for complete search history.

(56) References Cited

U.S. PATENT DOCUMENTS

| | | |
|---|---|---|
| 5,811,094 A | 9/1998 | Caplan et al. |
| 5,851,832 A | 12/1998 | Weiss et al. |
| 5,902,741 A | 5/1999 | Purchio et al. |
| 6,387,367 B1 | 5/2002 | Davis-Sproul et al. |
| 6,530,956 B1 | 3/2003 | Mansmann |
| 6,569,172 B2 | 5/2003 | Asculai et al. |
| 7,048,750 B2 | 5/2006 | Vibe-Hansen et al. |
| 7,137,989 B2 | 11/2006 | Asculai et al. |
| 7,148,209 B2 | 12/2006 | Hoemann et al. |
| 2002/0006428 A1* | 1/2002 | Mahmood et al. ............ 424/423 |
| 2003/0027330 A1 | 2/2003 | Lanza et al. |

FOREIGN PATENT DOCUMENTS

| | | | |
|---|---|---|---|
| EP | 1 282 690 | | 2/2003 |
| NL | EP 04075885.6 | * | 3/2004 |
| WO | WO-00/27999 | | 5/2000 |
| WO | WO-02/46401 | | 6/2002 |
| WO | WO-03/078609 | | 9/2003 |

OTHER PUBLICATIONS

"Cell Culture" and "Tissue Culture" Biology Online.org, accessed Oct. 8, 2009 2pgs <http://www.biology-online.org>.*
"manufactured." Merriam-Webster Online Dictionary. 2009. Merriam-Webster Online. Oct. 8, 2009 <http://www.merriam-webster.com/dictionary/manufactured>.*
International Search Report for PCT/NL2005/000207, mailed on Jul. 29, 2005, 5 pages.
Koerbling et al., New England Journal of Medicine (2003) 349(6):570-582.
Murphy et al., Arthritis and Rheumatism (2003) 48(12):3464-3474.
Tsuchiya et al., Materials Science Engineering C (2004) 24:391-396.
Barbero et al., Arthritis & Rheumatism (2003) 48(5):1315-1325.
Campbell et al., Biorheology (2006) 43:455-470.
Dell'Accio et al., Arthritis & Rheumatism (2001) 44(7):1608-1619.
Dell'Accio et al., Experimental Cell Research (2003) 287:16-27.
Mahmood et al., Biomacromolecules (2006) 7:3012-3018.
Saris et al., American Journal of Sports Medicine (2008) 36(2):235-246.
Woodfield et al., Biomaterials (2006) 27:1043-1053.
Ahmed et al., Tissue Engineering (2009) 15(3):665-673.
Bigdeli et al., Stem Cells (2009) 27:1812-1821.
Chen et al., Arthritis and Rheumatism (2009) 60(2):450-459.
Gan and Kandel, Tissue Engineering (2007) 13(4):831-842.
Grassel and Ahmed, Frontiers in Bioscience (2007) 12:4946-4956.
Hwang et al., PLoS ONE (2008) 3(6):e2498.
Miao et al., Artificial Cells, Blood Substitutes, and Biotechnology (2009) 37:214-221.
Mo et al., Bone (2009) 45(1):42-51.
Nicoll et al., Connective Tissue Research (2001) 42:59-69.
Song et al., Tissue Engineering (2005) 11(9/10):1516-1526.
Umeda et al., Journal of Orthopaedic Research (2009) 27:222-228.
Vadala et al., Spine (2008) 33(8):870-876.
Watanabe et al., Journal of Orthopaedic Research (2009) DOI 10.1002/jor.21036.
Yun-Feng et al., Journal of Clinical Rehabilitative Tissue Engineering Research (2008) 12(16):3185-3188.

* cited by examiner

*Primary Examiner* — Leon B Lankford
*Assistant Examiner* — Thane Underdahl
(74) *Attorney, Agent, or Firm* — Morrison & Foerster LLP

(57) ABSTRACT

The invention relates to the field of medical science, in particular to technology directed at repairing defects in living, preferably human, tissue. The present invention provides a method for inducing differentiation of multipotent cells to a desired cell type, as well as a method for repairing a tissue defect in a human or animal patient using the concept of said method for inducing differentiation of multipotent cells. The invention further relates to a kit for carrying out the method for repairing a tissue defect.

12 Claims, 4 Drawing Sheets

TISSUE REPAIR WITH MULTIPOTENT CELLS

CROSS-REFERENCE TO RELATED APPLICATION

This application is a U.S. National Phase of PCT/NL2005/000207, filed on 18 Mar. 2005, which claims priority to European patent application 04075885.6, filed on 18 Mar. 2004. The contents of said applications are incorporated herein in their entirety.

The invention relates to the field of medical science, in particular to technology directed at repairing defects in living, preferably human, tissue.

Primary cells are highly specialized cells present in the various specific types of tissue in an organism. They are involved in maintaining, repairing and supporting the function of said tissue.

In most situations where a defect occurs in living tissue, some intrinsic or extrinsic reaction is triggered. The primary cells that are present in the damaged tissue may produce specific growth and other factors which will be secreted to the surroundings of the defect. This is aimed at triggering proliferation of the still viable cells whereby the defect may become filled. Next, if necessary, the cells may differentiate into the required cell type to produce and maintain fully functional specialized tissue.

In many cases, however, the repair reaction of the body is not or not fully leading to a functional tissue. This may be due to a variety of reasons, such as the size of the defect, the poor availability of primary cells at the site of the defect to support the repair function, or the lack of influx from multipotent cells, which may differentiate to the required cell type, e.g. via the blood stream.

Articular cartilage covers the ends of long bones of synovial joints and consists of approximately 30% of extracellular matrix proteins and approximately 70% water. Chondrocytes are the only cell type found in normal articular cartilage but contribute less then 2% of the wet weight in human healthy adult tissue. The extracellular matrix consists predominantly of cartilage specific proteoglycon molecules with highly negatively charged sulfated glycosaminoglycan (GAG side chains, as well as type II collagen fibrils. The GAG side chains are able to bind water molecules, thereby sequestering water and generating an internal swelling pressure within the cartilage matrix. These hydrogel-like properties are essential for the interstitial fluid flow patterns observed inside the matrix during functional loading of cartilage, at which point water is forced out of the tissue to an amount that allows the negatively charged GAG chains to repel each other. Upon release of the compressive load, water is imbibed back into the tissue matrix. The collagenous network, together with water bound GAG, enables articular cartilage to withstand large compressive loads which gives the tissue its unique function in synovial joints: smooth and pain-free articulation, spreading of the applied load onto the subehondral bone and absorbing mechanical shocks.

Mature articular cartilage matrix is neither vascularized nor innervated, containing chondrocytes at low numbers which do not divide after skeletal maturity. It is partly for this reason that articular cartilage does not repair spontaneously or only to a very limited extent. Current approaches for cartilage repair rely on removal of tissue debris, access to the wound healing system of bone by penetrating the subehondral bone plate, and tissue transplantation and cell based therapies. Current clinical therapies are limited to autologous cell based therapies, such as autologous chondrocytes implantation (ACI) and mosaicplasty (also known as autologous osteochondral grafts). Due to severe drawbacks, both therapies can currently only address a limited share of the cartilage repair market.

For mosaicplasty, a major disadvantage is the limitation to small defects due to limited availability of donor tissue for transplantation. For ACI, drawbacks include the necessity to perform two surgical operations, high costs due to the required culturing of cells in vitro, and loss of phenotype of cartilage cells. Cartilage cells de-differentiate upon cell expansion, which is part of the ACI process. Hence, they require several months after surgery before they regain their original phenotype. Only then true cartilage repair can commence.

Recently, a second generation ACI has been developed involving autologous chondrocytes in a biomaterial matrix. This technique solves some of the problems of ACI, particularly the long and open surgical procedure that was required in ACI. However, three important drawbacks remain: two surgical procedures have to be carried out, high costs and long rehabilitation.

Accordingly, there is a need for further improvements in the field of repair of tissue defects, in particular for defects which are not, or not sufficiently repaired in a spontaneous fashion.

Figure 1:
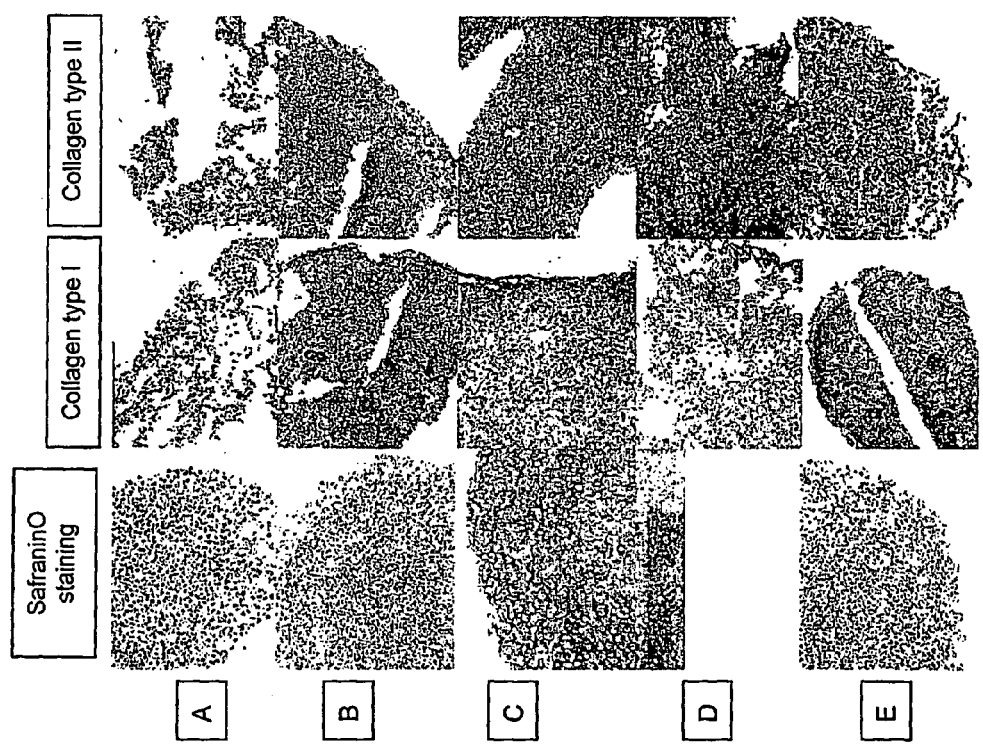
FIGS. 1A-E show results from safraninO staining and from immunostaining for Collagen type II and Collagen type I, performed on primary and expanded chondrocyte pellets as described in Example 1. Conditions for each panel were as follows: expanded cell pellets shared medium with primary cell pellets (A), expanded cell pellet cultured in conditioned medium by primary cell pellet (B), pellets of a 50/50 mixture of primary and expanded cells (C), +Control; primary cell pellet (D), −Control; expanded cell pellet (E).

In accordance with the invention it has been found that differentiation of multipotent cells may be induced by exposing them to primary cells. This effect has been observed even when primary cells are diluted with multipotent cells to considerable extent. Even at a very low number of primary cells relative to the number of multipotent cells differentiation of the multipotent cells into a specific lineage still takes place. In fact, it has been found that tissue repair proceeds faster when a population of primary and multipotent cells comprising 75 vol. % multipotent cells is used, than when a population of only primary cells is used.

Based on this finding, a method has been developed for repairing tissue defects which is highly cost-effective and does not suffer from the disadvantages outlined above for the prior art methods. The method according to the invention is defined in the appended claims.

In particular, a method for repairing a tissue defect according to the invention preferably no longer requires multiple surgical procedures. In one procedure, both primary and multipotent cells can be harvested and they can be applied to the tissue defect during the same procedure. Consequently, the treatment of one patient requires fewer resources in terms of time in operating facilities and in terms of medical staff. This will make it possible to treat a greater number of patients per year with the same medical staff and operating facilities then before. Also, the fact that only one surgical procedure suffices will significantly reduce the pain and suffering encountered by patients, as well as the risk of infections and other complications during surgery, and at the same time accelerate the procedure of recovery and rehabilitation.

It is to be noted that, in principle, it is known to use multipotent cells, such as mesenchymal stem cells, for tissue repair. Reference may be made in this regard to Mary Murphy et al., Arthritis & Rheumatism, 48(12), December 2003, pp. 3464-3474, and Körbling et al., N. Engl. J. Med., 349(6), August 2003, pp. 570-582. The studies disclosed in these papers explore the role that implanted stem cells may play in tissue repair or regeneration by delivery of a preparation of stem cells to a defect. In these studies, however, the stem cells were implanted by themselves, i.e. without primary cells.

The international patent application WO 03/078609 discloses a method for inducing differentiation of stem cells into a specific cell lineage. Unlike the present invention, the disclosed method always requires a culturing step of stem cells in the presence of a tissue sample in a suitable medium. In the method disclosed in said international patent application, the stem cells are differentiated into a cell lineage preferably chosen from the group of respiratory, prostatic, pancreatic, mammary, renal, intestinal, neural, skeletal, vascular, hepatic, haematopoietic, muscle or cardiac cell lineages. Differentiation of stem cells into chondrocytes to form cartilage tissue is not disclosed. Furthermore, nothing is disclosed about suitable ratios between stem cells and cells in the tissue sample.

In accordance with the invention, the term "multipotent cells" is intended to refer to cells that may still differentiate into various specialized types of tissue elements. Examples of multipotent cells are stem cells, including embryonic stem cells, progenitor cells, mesenchymal stem cells, bone marrow cells, or satellite cells. In accordance with the invention, fibroblasts are also considered to be encompassed by the term multipotent cells, as they have a capability to differentiate into other cell types. Bone marrow cells are preferably used.

In accordance with the invention, the term "primary cells" is intended to refer to cells which are specialized cells and which have lost the capability of further differentiation into (another) cell type. There are numerous examples of different types of primary cells in the human or animal body. According to the invention it is preferred to use are chondrocytes, nerve cells, osteoblasts, osteoclasts, hepatocytes, cardiomyocytes, myocytes, Schwann cells or urothelial cells as primary cells. In a highly preferred embodiment, the invention is directed to a method of cartilage repair and the primary cells are chondrocytes.

A method according to the invention involves the harvesting of a sample of multipotent cells and of a sample of primary cells. Typically, these samples will be obtained in a procedure referred to as a biopsy. This procedure is known per se and can be adapted to the specific type of tissue from which the sample of cells is to be taken. By way of example, a cartilage tissue biopsy, containing chondrocytes, of at least 100 mg (involving 5 to 6 biopsies with a 4 mm diameter) may be taken from a, preferably uninvolved low-load bearing, area of an injured knee during arthroscopy and collected in a tube containing a suitable medium, or directly subjected to a peroperative cell isolation protocol. Bone marrow autopsies can be obtained from either the pelvic bone (iliac crest) or either the proximal or distal part of the femur. All biopsies preferably are taken from an area where, or close to where, the intended surgery is to take place. When openings in the bone are created as part of the procedure, a 8 gauge biopsy needle may be inserted and 2-50 cc of bone marrow may be aspirated. Preferably, the needle and syringe used are flushed beforehand using a 1% heparin solution to prevent the marrow from clotting. In case whole bone marrow is used, this is preferably aspirated without heparin. After aspiration, the bone marrow may be injected under sterile conditions into a heparinized tube, e.g. for every 10 ml of bone marrow.

In an alternative embodiment, a biopsy, particularly a biopsy of multipotent cells, involves making available multipotent cells during surgery at the site of the defect. In accordance with this embodiment, multipotent cells are used which are present at or close to the tissue defect. Advantageously, this embodiment does not require isolating the multipotent cells from the patient's body; they are merely made available to the primary cells at the site of the defect. This may be done, for instance, by recruiting multipotent cells in situ by subchondral bone plate penetration, or by applying chemo attractants to attract multipotent cells from synovial origin to the defect.

The type and source of the primary cells will be chosen dependent on the type of tissue that is intended to be repaired. Preferably, the primary cells are of a cell type that naturally occurs in the tissue that will be repaired. In a highly preferred embodiment, chondrocytes are harvested for repair of cartilage defects. The type and source of multipotent cells is preferably also chosen dependent on the type of tissue that is intended to be repaired.

The following overview gives examples of how cell types of primary and multipotent cells may be selected with a view to repair of a specific tissue type.

| Repair tissue | Primary cell source | Multipotent cell source |
|---|---|---|
| Bone | osteoblasts from trabecular bone in long bone, pelvic bone, clavicula, compact, subchondral bone | Bone marrow, mesenchymal stem cells, stem cells from i.e. fat, skeletal muscle, progenitor cells, umbilical cord cells, fibroblasts, human bone marrow stromal cells, vascular derived cells, synovial cells, dermal fibroblast and hair follicle stem cells, and cells from periosteum or perichondrium |
| Cartilage | Chondrocytes derived from nose, knee or hip joint, elbow, ear, ankle or trachea cartilage, isolated chondron | |
| Liver | Hepatocytes from liver | |
| Heart, Heart valves | Cardiomyocytes from hart muscle, vascular myofibroblasts form vascular tissue in the hart | |

-continued

| Repair tissue | Primary cell source | Multipotent cell source |
|---|---|---|
| Muscle | Myocytes from smooth muscle | |
| Nerve | Schwann cells, neural cells from epineurial tubes | |
| Bladder | Urothelial cells from urological tract | |
| Intestine | Cells from jejunum, duodenum | |
| Ligaments and Tendons | Cells from cruciate ligaments or tendon | |
| Hair | Cells from hair follicle, such as dermal papilla cells, outer root sheath or matrix epithelial cells | |

In a preferred embodiment, the harvested cells are isolated from the samples obtained in the biopsy. This may be done for cells in a fluid by magnetic flow sorting, fluorescence activated cell sorting (FACS), column filtration, centrifugation, percoll separation, or attachment to tissue culture plastic. For cells in tissue this may be done by triturating, i.e. dispersing of cells through mild pumping action, followed by dissection and enzymatic digestion of tissue, and isolation via column filtration, centrifugation, membrane separation, or gel separation. Suitable examples of enzymes to be used in this respect include, but are not limited to collagenase, dispase, trypsin, elastase, hyaluronidase, and papain.

It is also possible to use harvested cells without isolating them. For instance, fractions of bone marrow or whole bone marrow may be used directly to provide multipotent cells. Also, minced or chopped tissue (tissue chips) may be used without further cell isolation as primary cell component.

In accordance with the invention, the obtained populations of multipotent and primary cells are combined in vitro, in vivo or in situ in order to induce differentiation of the multipotent cells. Both the multipotent and the primary cells may be combined with one another with or without components of tissue which would be surrounding them in their natural environment. Examples of such components include bone marrow and blood. Advantageously, the multipotent cells will differentiate into the cell type of the primary cells. Surprisingly, it has been found that only a small number of primary cells, relative to the number of multipotent cells, are necessary to achieve the desired effect of induction. The ratio of the number of cells in the population of primary cells to the number of cells in the population of multipotent cells, which two populations are to be combined, is preferably from 1:200 to 2:3, more preferably from 1:100 to 1:3, even more preferably from 1:50 to 1:5.

In J. Thorac. Cardiovasc. Surg., June 2003, 125(6), pp. 1470-1480, and J. Thorac. Cardiovasc. Surg., August 2002, 50(8), pp. 321-324, Fukuhara et al. have described that bone marrow stromal cells may go into cardiac lineage in vitro when co-cultured together with cardiomyocytes in a ratio of 1:1 for seven days. Surprisingly, in accordance with the invention it has been found that far smaller numbers of primary cells relative to the number of multipotent cells suffice in order to induce differentiation of the multipotent cells. Also, in accordance with the invention, co-culturing in vitro of the combined cell populations is not necessary. In fact, it is preferred that the combined cell populations are applied to a tissue defect without culturing in vitro, be it before or after combining the two populations of cells.

Conventional approaches to tissue engineering starting from multipotent cells relied on chemical factors, such as growth factors, in order to stimulate and achieve differentiation of the multipotent cells. In these approaches, the multipotent cells are subjected to the action of the chemical factors in vitro to be implanted only after differentiation. As already mentioned, in accordance no in vitro culturing is necessary. Instead the harvested multipotent cells may be applied to a tissue defect in undifferentiated state. Also, in accordance with the invention the use of chemical factors in order to achieve differentiation of multipotent cells is not necessary. Nonetheless, differentiation may be further enhanced by making use of such factors, which is also encompassed by the invention. Some examples of chemical factors that can be used include cell adhesion factors such as vitronectin, tenascin, RGD peptides, hyaluronan, laminin, pronectin, or fibronectin or fragments thereof, e.g. arginine-glycine-aspartate, and cytokines or other releasable cell stimulating factors such as basic fibroblast growth factor (bFGF), transforming growth factor beta (TGF-beta), nerve growth factor (NGF), insulin-like growth factor-1 (IGF-1), growth hormone (GH), multiplication stimulating activity (MSA), cartilage derived factor (CDF), bone morphogenic proteins (BMPs), growth differentiation factor-5 (GDF-5), dexamethasone (dex), or other osteogenic factors, anti-angiogenesis factors (angiostatin), and platelet derived growth factor (PDGF).

For induction of differentiation of multipotent cells into chondrocytes, the use of fibronectin has been found to be particularly advantageous. Fibronectin is generally known to inhibit chondrogenesis (West, C. M., R. Lanza, J. Rosenbloom, M. Lowe, H. Holtzer, and N. Avdalovic, *Fibronectin alters the phenotypic properties of cultured chick embryo chondroblasts*. Cell, 1979. 17(3): p. 491-501, Pennypacker, J. P., J. R. Hassell, K. M. Yamada, and R. M. Pratt, *The influence of an adhesive cell surface protein on chondrogenic expression in vitro*. Exp Cell Res, 1979. 121(2): p. 411-5). In contrast and surprisingly, it has now been found that fibronectin enhances cartilage formation (FIG. 4) in a method according to the invention. Without wishing to be bound by theory, it is postulated that one of the causes for this enhancement of cartilage formation may be that fibronectin allows chondrocytes to maintain their rounded morphology.

Before or after combining the populations of primary and multipotent cells, they may be seeded onto a biocompatible scaffold. Preferably, the populations are combined in a manner suitable to secure a homogeneous distribution of the two cell types over the combined cell population. In this regard, it is preferred that the populations are combined before they are seeded onto the scaffold. On the other hand, it is also feasible, and under certain conditions advantageous, to distribute the two cell types in a compartmental fashion over the scaffold, such that distinct compartments comprising predominantly, or even exclusively cells of one cell type.

Whether or not it is desirable to use a biocompatible scaffold in a certain situation can be readily determined by the person skilled in the art depending on the type of tissue that is in need of repair and the size of the defect. Particularly for repair of larger defects in tissues, such as bone or cartilage, which have a mechanical, e.g. load bearing, function, the use of a scaffold is beneficial. The choice for material for the scaffold will also depend on the type of tissue involved. Suitable examples of materials include metals and metal alloys, ceramics, (bio)glasses and polymeric materials. It is of course important that the material is biocompatible, which means that the material may be incorporated into a human or animal body substantially without unacceptable responses of the human or animal.

Preferred materials used in the manufacture of a scaffold are biocompatible, bioresorbable over periods of weeks or longer, and generally encourage cell attachment. The term "bioresorbable" is used herein to mean that the material degrades into components which may be resorbed by the body and which may be further biodegradable. Biodegradable materials are capable of being degraded by active biological processes such as enzymatic cleavage. Other properties desirable for materials to be used in the manufacture of the devices described herein include solubility in a biologically acceptable solvent that can be removed to generally accepted safe levels, and elasticity and compressive and tensile strength.

Natural polymers which are suitable include polysaccharides such as cellulose, dextrans, chitin, chitosan, glycosaminoglyeans; hyaluronic acid or esters, chondroitin sulfate, and heparin; and natural or synthetic proteins or proteinoids such as elastin, collagen, agarose, calcium alginate, fibronectin, fibrin, laminin, gelatin, albumin, casein, silk protein, proteoglycans, Prolastin, Pronectin, or BetaSilk. Mixtures of any combination of polymers, as well as chemically modified derivatives of the mentioned polymers may also be used.

Synthetic polymers which have been found to be particularly suited for making a scaffold include copolymers of polyalkylene glycol and aromatic esters and poly(alpha)esters, such as: poly(lactic acid) (PLA) and poly(DL-lactic-co-glycolic acid) (PLGA). Other suitable materials include: thermoreversible or photocurable gels, such as pluronic or block copolymers of poly(D-lactide) and a poly(L-lactide) grafted dextran, preferably comprising a polyester or a poly-α-amino acid backbone, and/or heparin, poly(epsilon.-caprolactone) (PCL), polyanhydrides, polyarylates, and polyphosphazene. Preferred synthetic polymers include: poly(hydroxy alkanoates), polydioxanone, polyamino acids, poly(gamma-glutamic acid), poly(vinyl acetates), poly(vinyl alcohols), poly(ethylene-imines), poly(orthoesters), polypohosphoesters, poly(tyrosine-carbonates), poly(ethylene glycols), poly(trimethlene carbonate), polyiminocarbonates, poly(oxyethylene-polyoxypropylene), poly(alpha-hydroxy-carboxylic acid/polyoxyalkylene), polyacetals, poly(propylene fumarates), and carboxymethylcellulose.

In a highly preferred embodiment, the scaffold is formed of a specific class of polymeric materials having hydrogel properties. This is the class of copolymers of a polyalkylene glycol and an aromatic polyester. Preferably, these copolymers comprise 40-80 wt. %, more preferably 50-70 wt. % of the polyalkylene glycol, and 60-20 wt. %, more preferably 50-30 wt. % of the aromatic polyester. A preferred type of copolymers according to the invention is formed by the group of block copolymers. Preferred polyalkylene glycols are chosen from the group of polyethylene glycol, polypropylene glycol, and polybutylene glycol and copolymers thereof, such as poloxamers. A highly preferred polyalkylene glycol is polyethylene glycol. Preferred polyesters are chosen from the group of polyethylene terephtalate, polypropylene terephtalate, and polybutylene terephtalate. A highly preferred polyester is polybutylene terephtalate.

Preferably, the polyalkylene glycol has a weight average molecular weight of from 150 to 10,000, more preferably of 200 to 1500. The aromatic polyester preferably has a weight average molecular weight of from 200 to 5000, more preferably of from 250 to 4000. The weight average molecular weight of the copolymer preferably lies between 20,000 and 200,000, more preferably between 50,000 and 120,000. The weight average molecular weight may suitably be determined by gel permeation chromatography (GPC). This technique, which is known per se, may for instance be performed using tetrahydrofuran as a solvent and polystyrene as external standard.

The scaffold will be constructed to achieve a favorable mechanical stability and proliferation and differentiation (both in vivo). Of course, the scaffold should also be of a size and shape to fit into the defect that is to be repaired. It is envisaged that a standard size and shape, or a combination of standard sizes and shapes are supplied to a surgeon who can mould or adapt the shape and size to the requirements of the defect to be treated. It is also possible that the scaffold does not have a particular shape but enables the combined populations of multipotent and primary cells to be injected, e.g. in the form of an injectable gel. Variables that can be manipulated to achieve a desired effect are inter alia macrostructure, chemical composition, microstructure including porosity, pore size (diameter), surface modifications such as surfactants and cell attachment peptides, incorporation of bioactive agents, flow properties (e.g. channels that direct and control fluid flow through and within the scaffold), and structural elements on or in the scaffold.

Often, the scaffold will have a porous or fibrous structure in order to facilitate transport of nutrients to the cells seeded onto it, and of waste materials from the cells seeded onto and/or into it. A porous structure of a polymeric material may be obtained by any known method, such as salt leaching or sintering. In principle, any combination of techniques, such as phase inversion, freeze drying and salt leaching may be used. It is also possible to employ a scaffold which is manufactured in a free form, rapid prototyping or 3D-printing process.

In a preferred embodiment, the outer surface of the scaffold is partly or completely provided with a ceramic coating. Preferably, the ceramic coating is a calcium phosphate coating, e.g. a coating comprising octacalcium phosphate, an apatite, such as hydroxyapatite or carbonate apatite, a whitlockite, such as α-tricalcium phosphate, β-tricalcium phosphate, sodium calcium phosphate, or a combination thereof. It is also possible to use a scaffold which is a biphasic composite structure of a ceramic material and a polymeric material. It has been found that the presence of ceramic material is highly beneficial as it can be used to mimic the properties of bone.

The seeding of the cell populations may be carried out in any known manner, for instance by using a seeding vehicle, static, dynamic or perfusion seeding, or a combination thereof.

After combining the populations of primary and multipotent cells, they are applied to the defect. It is one of the advantages of the invention that no expansion via culturing of the cells in vitro is involved. The primary and multipotent cells will be made available to the defect site to induce and support the natural repair reaction of the body. Without wishing to be bound by theory, it is believed that the primary cells produce and secrete specific factors as a response to their natural surroundings, which factors will enhance or induce differentiation of the multipotent cells into a tissue specific lineage. Thus, by applying primary cells, the multipotent cell population is provided with a 'factory' that establishes a natural cascade of growth and other factors involved in tissue repair.

As already indicated above, it is preferred that the two populations of cells are substantially homogeneously distributed throughout each other before application to the defect. This may be achieved by resuspension of the mixture of the two populations of cells through rotation or decanting, preferably just prior to application. In case the combined populations of cells are to be applied to the defect together with a scaffold, they are preferably combined first and then seeded onto the scaffold. The scaffold comprising the combined cell populations may then be applied to the defect.

The manner in which the combined populations of cells will be applied to the defect will depend on the type of tissue in which the defect exists and on whether or not a scaffold is used. Suitable manners of applying the cells include neat (i.e. cells only), direct in-gel or tissue-glue for application at sites requiring no immediate mechanical stability, or in-gel or tissue-glue seeding onto a scaffold for application at sites that do. Seeding of cells onto a scaffold, or their application to the site of tissue repair, may be assisted by using an aggregation factor, such as fibronectin or vitronectin. The cells can also be applied under periosteum sutured over the tissue defect and closed with fibrin glue. Factors such as hyaluronan, glycosaminoglycans, or inhibitors of cell apoptosis may be added to enhance cell survival after implantation, when deemed useful.

The invention further encompasses a kit for carrying out a method as described above. The kit preferably provides the medical staff all the materials and equipment necessary to carry out the present procedure for tissue repair. Thus, a kit according to the invention comprises means for taking a biopsy of a population of primary cells, means for taking a biopsy of a population of multipotent cells, and means for applying a combination of both populations to a tissue defect. In a preferred embodiment, the kit further comprises a biocompatible scaffold, as described above, and means for seeding the combined populations of multipotent and primary cells onto the scaffold. It is further preferred that the kit comprises means for isolating the cells from a biopsy.

Examples of devices or equipment for taking a biopsy of a population of multipotent cells include aspirate needles and syringes, preferably including a 8 gauge biopsy needle for bone marrow biopsies.

Examples of devices or equipment for taking a biopsy of a population of primary cells include, depending on the type of primary cells, a small diameter ring curette (preferably at most 6 mm), or a Notchplasty gouge.

Suitable means or instruments for isolating cells, i.e. multipotent and primary cells, from a biopsy are inter alia enzymes, such as collagenase, hyaluronidase, elastase, papain, trypsin, or dispase.

The kit preferably also comprises means for combining and mixing the populations of multipotent and primary cells. To this end, instruments such as a cell strainer, plasticware for cell processing, a cell filter system and one or more pipettes may be present.

Suitable means for seeding cells onto a scaffold that may be present in a kit according to the invention include simple seeding devices such as a confined or unconfined chamber, or perfusion system.

Examples of means for applying the combined populations of multipotent and primary cells, or the scaffold with the combined populations of multipotent and primary cells seeded thereon to a tissue defect, that may be present in a kit according to the invention include tissue glue, gels, cell aggregation factors and one or more syringes.

The invention will now be further elucidated by the following, non-restrictive examples.

EXAMPLE 1

Inducing Differentiation by Mixing Primary and Expanded Chondrocytes in Pellet Culture Assay Under Different Conditions Chondrocytes were isolated from adult bovine cartilage from the tibia by means of collagenase type II (Worthington) digestion. Isolated cells were seeded at a density of 3500 cells/cm$^2$ and subcultured for 3 passages in medium containing DMEM, 10 mM HEPES, 1× Non Essential amino acids, 0.2 mM ASAP, 100 U penicillin, 100 µg/ml streptomycin, 0.4 mM proline and 10% FBS at 37° C./5% $CO_2$. With reference to FIG. 1, primary and expanded cells were cultured in pellet assay under following conditions; expanded cell pellets shared medium with primary cell pellets (A) expanded cell pellet cultured in conditioned medium by primary cell pellet (B). Pellets of a 50/50 mixture of primary and expanded cells (C). +Control; primary cell pellet (D) –control; expanded cell pellet (E). After 2 wks in culture, pellets were fixated with 1.5% glutaric aldehyde in cacodylate buffer (0.14M/pH 7.2-7.4) for safraninO staining, embedded and frozen in OCT compound (Tissue-Tek) for immunostaining or frozen at −80° C. for quantitative GAG and DNA assay. Sulphated Glycosaminoglycans (GAG) were stained with safraninO and counterstained with haematoxylin and fast green respectively for nuclei and cytoplasm. Cryosections were fixated with aceton and stained for Collagen type II (1:100, DSHB II-II6B3) or Collagen type I (1:1000, Ab-1, Calbiochem). Blocking was done with 10% human serum and as a secondary goat anti-mouse antibody (1:100, DAKO) was used. Staining was visualized with DAB-solution (DAKO) for 10 minutes.

SafraninO and collagen type II results in FIG. 1 show that cells in group C and D produce cartilage specific GAG throughout the pellet whereas pellets of group A, B and E do not produce GAG at all. Immunochemical results in FIG. 1 also show that only cells in the outer ring of a pellet from group C and D express Collagen type I, confirming differentiation of cells in mixed cell pellet (C) to be at comparable levels as in pellet of primary cells only. Whereas collagen type I staining of pellets in group A, B and E is found throughout the pellets, no specific collagen type II can be found in pellet of these groups. Thus it is concluded that expanded chondrocytes are not stimulated to differentiate, hence produce cartilage specific extracellular matrix, by culturing in either shared medium with primary cells or primary cell conditioned medium. However when in cell-cell contact with primary cells these results show that differentiation is stimulated and GAG's are produced at comparable levels in pellets of mixed primary and expanded cells to primary cells only. With these results it is shown that cell-cell contact induces differentiation.

EXAMPLE 2

Differentiation in Pellets Consisting of a Primary and Expanded Cell Mixture at Several Ratio's Experiment was designed to examine the differentiation capacity of different primary/expanded ratios in pellet assay.

Chondrocytes were isolated from adult bovine cartilage from the tibia by means of collagenase type II (Worthington) digestion. Isolated cells were seeded at a density of 3500 cells/cm$^2$ and subcultured for 3 passages in medium containing DMEM, 10 mM HEPES, 1× Non Essential amino acids, 0.2 mM AsAP, 100 U penicillin, 100 µg/ml streptomycin, 0.4 mM proline and 10% FBS at 37° C./5% $CO_2$. Pellets of a 50/50 mixture of primary and expanded cells were cultured in medium described above. After 2 wks in culture, pellets were fixated with 1.5% glutaaraldehyde in cacodylate buffer (0.14M/pH 7.2-7.4) for safraninO staining, embedded and frozen in OCT compound (Tissue-Tek) for immunostaining or frozen at −80° C. for quantitative GAG and DNA assay. Sulphated Glycosaminoglycans (GAG) were stained pink with safraninO and counterstained with haemtoxylin and fast green respectively for nuclei (brown) and cytoplasm (blue). Cryosections were fixated with aceton and stained for Collagen type II (1:100, DSHB II-II6B3) or Collagen type I (1:1000, Ab-1, Calbiochem). Blocking was done with 10% human serum and as a secondary goat anti-mouse antibody (1:100, DAKO) was used. Staining was visualized with DAB-solution (DAKO) for 10 minutes. Samples for quantitative GAG and DNA assay were digested with 50 mg/ml proteinase K (SIGMA) for >16 hrs at 56° C. GAG content was spectrophotometrically determined with 9-dimethylmethylene blue chloride (DMMB) staining in PBE buffer (14.2 g/l $Na_2HPO_4$ and 3.72 g/l $Na_2EDTA$, pH 6.5) and DNA assay was done with CyQuant DNA assay according to the manufacturer description.

Figure 2:
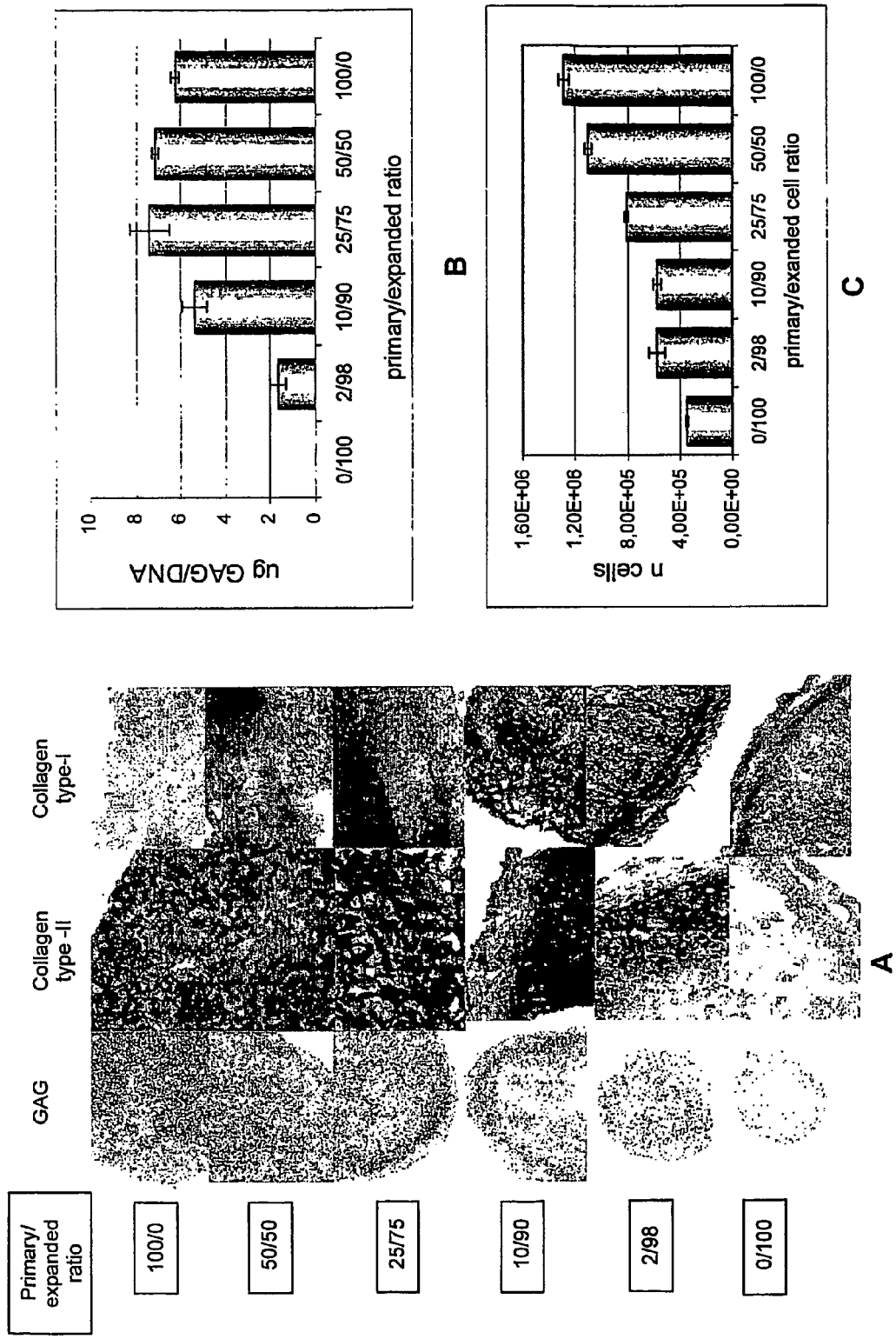
FIGS. 2A-C show results from a pellet assay on primary/expanded cells mixed at indicated ratios, described in Example 2. Panel A shows qualitative staining for Sulphated Glycosaminoglycans (GAG) and Collagen types I and II. Panel B shows quantitative GAG/DNA results. Panel C shows cell number results.

With reference to FIG. 2 primary/expanded cells were mixed at indicated ratios and cultured in pellet assay (500.000 cells/pellet) for 2 wks. Qualitative GAG and Collagen type II results show that only in pellets with 0/100 primary/expanded cells no GAG or collagen type II can be found while only in pellets with 100/0 primary/expanded cells collagen type I is shown to be present. With these results that with decreasing amounts of primary cells the level of differentiation is maintained throughout the pellets (A). Moreover, quantitative GAG/DNA results (B) show that when amount of primary cells is decreased to 10%, differentiation is still at comparable levels as with primary cells only in pellet culture assay. Moreover, when number of primary cells is further decreased to 2% the amount of GAG/DNA is approximately 25× higher then expected from the same amount of primary cells only. Surprisingly, cell number results show that only when the amount of primary cells in the pellet is rising above 25%, proliferation occurred.

With these results it is shown that in a cell mixture of primary/expanded chondrocytes differentiation is stimulated even when the amount of primary cells is decreased to 2% of the total cell population. Quantitative GAG/DNA results actually show that amount of GAG in pellets containing 2% primary cells is approximately 25× higher then can be expected from the same amount of primary cells alone. With these data it is shown that differentiation is strongly enhanced by a small amount of primary cells in the presence of a large amount of dedifferentiated cells such as cultured chondrocytes.

EXAMPLE 3

Figure 3:
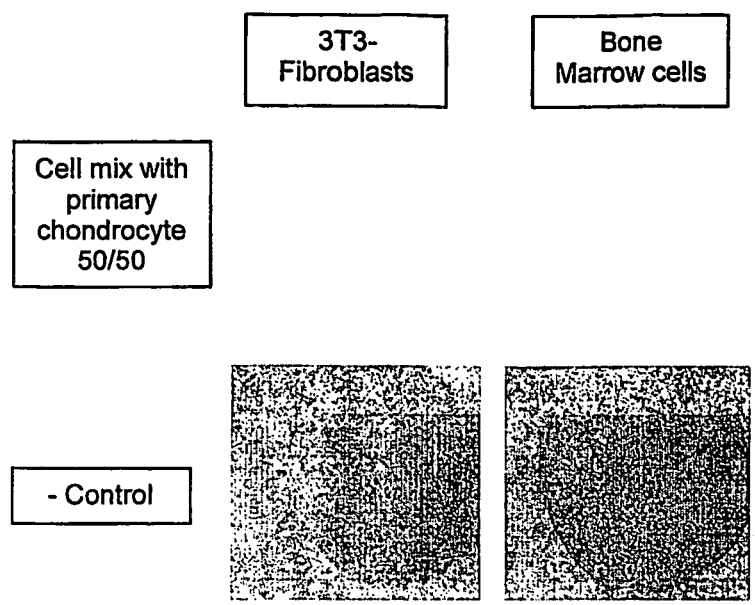
FIG. 3 shows results from cell pellet assays using mixtures of 50% primary cells and 50%, respectively, of fibroblasts or bone marrow cells, with sections of pellets stained for Sulphated Glycosaminoglycans (GAG) with safraninO, as described in Example 3.

Differentiation of Respectively Fibroblast/Primary Chondrocyte and Bone Marrow Cells/Primary Chondrocytes in Pellet Assay Experiment was designed to examine the differentiation capacity of different multipotent cell types mixed with primary chondrocytes in pellet assay. Fibroblast were from a 3T3 fibroblasts cell line and cultured in DMEM (BioWhitaker #BE12-604F) 100 U/ml penicillin, 100 μg/ml streptomycin and 5% FBS and bone marrow cells were isolated from human bone marrow biopsy and cultured in αMEM (Gibco #22571-020) containing 10% FBS, 100 U/ml penicillin, 100 μg/ml streptomycin and 10 mM AsAP and 1 ng/ml bFGF. Chondrocytes were isolated from a biopsy of human articular cartilage from the knee. After mixing pellets were cultured at 37° C./5% $CO_2$ in medium containing DMEM (Gibco #41965-039), 10 mM HEPES, 1× Non Essential amino acids, 0.2 mM ASAP, 100 U penicillin, 100 μg/ml streptomycin, 0.4 mM proline and 10% FBS. With reference to FIG. 3 cell mixtures of 50% primary cells and 50% of respectively fibroblasts or bone marrow cells were centrifuged to form pellets and cultured for 3 wks. Sections of pellets were stained for Sulphated Glycosaminoglycans (GAG's) with safraninO (pink). Results show production of GAG's throughout the pellets when chondrocytes were mixed with either 3T3-fibroblast or bone marrow cells but not in pellets of fibroblasts or bone marrow cells only. Indicating stimulation of differentiation into a cartilage lineage with either fibroblasts or bone marrow cells (multipotent cells) when mixed with primary chondrocytes.

EXAMPLES 4 & 5

Differentiation of Primary/Expanded Cell Mix on PEGT/PBT 300/55/45 Scaffolds In Vivo Experiment was designed to examine the differentiation capacity of different primary/expanded cell mixtures on a porous scaffold in vivo either or not in the presence of a factor involved in aggregation of cells (fibronectin).

Chondrocytes were isolated from a biopsy of human articular cartilage from the knee by means of collagenase type II (Worthington) digestion. Isolated cells were seeded at a density of 3500 cells/cm$^2$ and subcultured for 3 passages in medium containing DMEM, 10 mM HEPES, 1× Non Essential amino acids, 0.2 mM AsAP, 100 U penicillin, 100 μg/ml streptomycin, 0.4 mM proline and 10% FBS at 37° C./5% $CO_2$. Primary cells were isolated from mature bovine cartilage and combined with expanded cells at the following ratios: 0/100, 100/0, and 2/98, 20/80 and 50/50. Cell mixtures were incubated for 1 hr with 300 ug/ml fibronectin to form aggregates and seeded dynamically onto porous scaffolds for 24 hrs in eppendorf tubes with a gas exchange filter at 37° C./5% $CO_2$ in culture medium. Porous scaffolds were made of segmented copolymers of poly(ethylene glycol) terephtalate (PEGT) and poly(butylene terephtalate) (PBT) with the composition of 55/45 PEGT/PBT weight ratio and a molecular weight of 300 for PEG. After 7 days static culturing in culture medium described above, seeded scaffolds were implanted subcutaneously in nude mice. For each experimental group 8 scaffolds were implanted and for controls 6. After 4 wks scaffolds were explanted and weight ratio of the whole and ½ of each scaffolds was determined for quantitative glycosamino glycan (GAG) and DNA analysis. Half of the scaffold was digested with 50 mg/ml proteinase K (SIGMA) for >16 hrs at 56° C. GAG content was determined with 9-dimethylmethylene blue chloride (DMMB) staining in PBE buffer (14.2 g/l $Na_2HPO_4$ and 3.72 g/l $Na_2EDTA$, pH 6.5) in a spectrophotometer (540 nm) and DNA assay was done with CyQuant DNA assay according to the manufacturer description.

Figure 4:
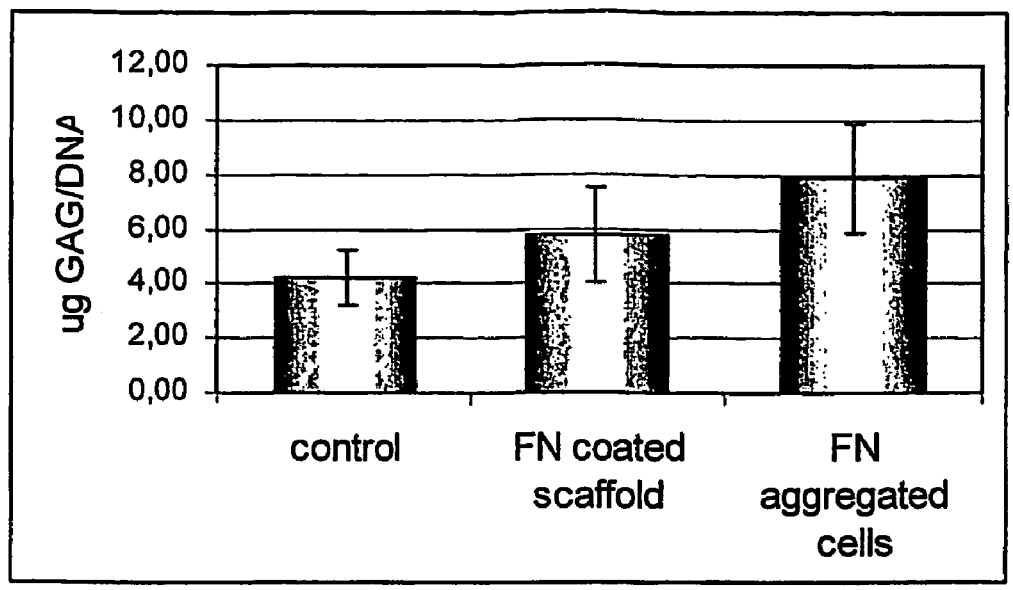
FIG. 4 shows GAG/scaffold quantification results obtained following seeding of cell mixtures with 50/50 primary/expanded ratio onto scaffolds and subcutaneously implanting the scaffolds in nude mice, with samples explanted and GAG/scaffold quantified after 4 wks., as described in Examples 4 and 5. "Control"=untreated cell mixture seeded onto untreated scaffold; "FN coated scaffold"=untreated cell mixture seeded onto fibronectin (300μ/ml) coated scaffold; "FN aggregated cells"=fibronectin treated cell mixture (300μ/ml) seeded onto untreated scaffolds.

With reference to FIG. 4 cell mixtures with 50/50 primary/expanded ratio were seeded onto porous (Mw PEG)/(w/w PEGT/PBT) 300/55/45 scaffolds. Untreated cell mixture was seeded onto untreated scaffold (control), Untreated cell mixture was seeded onto fibronectin (300 μg/ml) coated scaffold (FN coated scaffold) or fibronectin treated cell mixture (300 μg/ml) were seeded onto untreated scaffolds (FN aggregated cells). Scaffolds were subcutaneously implanted in nude mice and after 4 wks samples were explanted and GAG/scaffold was quantified. Results show that aggregation of cells in the presence of fibronectin increases GAG/DNA production of 50/50 primary/expanded cell mixture.

Figure 5:
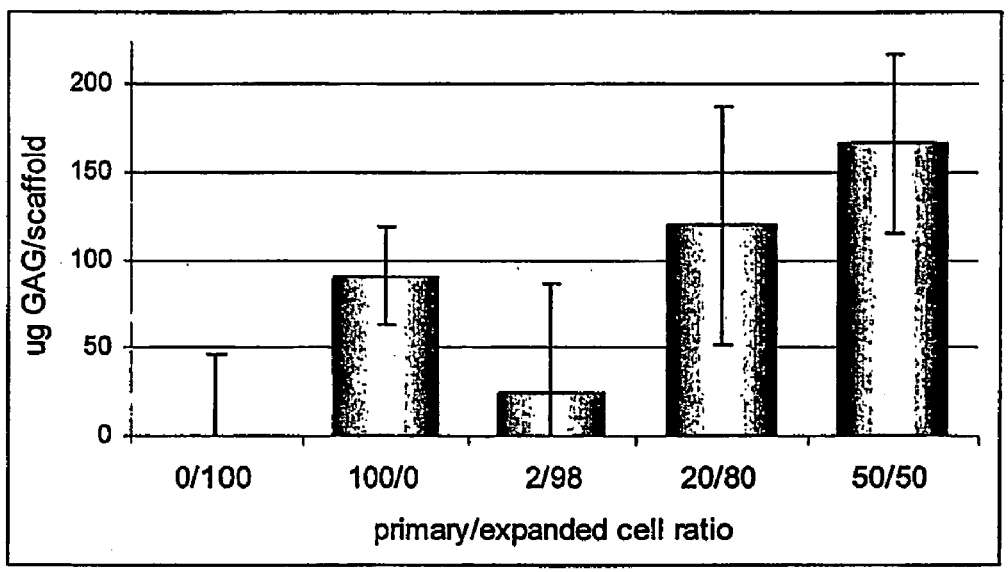
FIG. 5 shows results from GAG/scaffold quantification following aggregation of cell mixtures with different primary/expanded ratios in the presence of 300μ/ml fibronectin and seeding onto porous (Mw PEG)/(w/w PEGT/PBT) 300/55/45 scaffolds, which were subcutaneously implanted in nude mice, with samples explanted and GAG/scaffold quantified after 4wks., as described in Examples 4 and 5.

With reference to FIG. 5 cell mixtures with different primary/expanded ratios were aggregated in the presence of 300 μg/ml fibronectin and seeded onto porous (Mw PEG)/(w/w PEGT/PBT) 300/55/45 scaffolds. Scaffolds were subcutaneously implanted in nude mice and after 4 wks samples were explanted and GAG/scaffold was quantified. Results show that in the presence of 20% primary cells the GAG/scaffold content is equal to scaffolds with 100% primary cells. Moreover when 50% of primary cells are mixed with 50% expanded cells the GAG/scaffold content increased >1.5.

In FIG. 5, μg GAG/scaffold shown is normalized to 0/100 cell ratio by subtracting a constant value. Media conditioned by primary cells were shown ineffective in inducing chondrogenesis in multipotent cells.

Fibronectin is generally known to inhibit chondrogenesis. In contrast and surprisingly, it found that fibronectin enhanced cartilage formation (FIG. 4) within the said induction system.

To retain cells within the defect site, in particular for an interoperative and autologous procedure, preferentially, specific measures are taken or required, ie using gels or other means to immobilize cells without relying on cell attachment onto a substrate requiring a substantial time period.

To protect cells from joint loading postsurgery, preferentially, cells will be surrounded by a scaffold or gel or other means which provide some or full mechanical support. For cartilage repair, preferentially, the scaffold used is mechanically functional, i.e. it shows similarities to mechanical properties of cartilage.

From these results it is clear that differentiation capacity of primary/expanded cell mixtures of 20/80 in porous scaffolds in vivo is equal to primary cells alone.

In these examples, cells were treated with fibronectin to illustrate differentiation can be supported by aggregation of cells. To aggregate cells other tissue specific factors as vitronectin, laminin, hyaluronan can be used. The scaffold chosen for this study is an example of a scaffold suitable to support mechanical properties of a specific tissue, in this case cartilage, immediately after implantation. In this example the chosen scaffold is also used as a vehicle to apply a cell mixture into the defect.

The invention claimed is:

1. A method for repairing a cartilage tissue defect in a human or animal patient comprising:
    (a) taking a population comprising multipotent cells selected from the group consisting of mesenchymal stem cells, bone marrow cells, and expanded chondrocytes;
    (b) taking a biopsy comprising a population of primary chondrocytes;
    (c) combining the population comprising multipotent cells and the population of primary chondrocytes; and
    (d) applying the combined populations comprising multipotent cells and primary chondrocytes to the cartilage tissue defect, wherein the ratio of the number of cells in the population of primary chondrocytes to the number of cells in the population comprising multipotent cells is from 1:200 to 1:3.

2. The method of claim 1, wherein the population of multipotent cells and/or the population of primary chondrocytes are isolated from the biopsy.

3. The method of claim 1, wherein the multipotent cells and the primary chondrocytes are human cells.

4. The method of claim 1, wherein the multipotent cells are bone marrow cells.

5. The method of claim 1, wherein the ratio of the number of cells in the population of primary chondrocytes primary cells to the number of cells in the population of multipotent cells is from 1:50 to 1:5.

6. The method of claim 1, wherein the population of multipotent cells and the population of primary chondrocytes are combined without having been expanded in vitro.

7. The method of claim 1, wherein the combined populations of multipotent and primary chondrocytes are applied to the cartilage tissue defect without having been expanded in vitro.

8. The method of claim 1, wherein the population of multipotent cells and the population of primary chondrocytes are provided on a biocompatible scaffold.

9. The method of claim 8, wherein the biocompatible scaffold is manufactured of a material selected from the group consisting of metals and metal alloys, ceramics, (bio)glasses, natural and synthetic polymeric materials, and combinations thereof.

10. The method of claim 9, wherein the biocompatible scaffold comprises a copolymer of a polyethylene glycol and a polybutylene terephthalate.

11. The method of claim 10, wherein the biocompatible scaffold is partially or completely covered by a calcium phosphate coating.

12. The method of claim 8, wherein the population of multipotent cells and the population of primary chondrocytes are seeded on the biocompatible scaffold without having been expanded in vitro.

* * * * *